United States Patent [19]
Amaral et al.

[11] Patent Number: 5,807,740
[45] Date of Patent: Sep. 15, 1998

[54] REGULATORS OF UCP2 GENE EXPRESSION

[75] Inventors: M. Catherine Amaral; Jin-Long Chen, both of Souh San Francisco, Calif.

[73] Assignee: Tularik Inc., South San Francisco, Calif.

[21] Appl. No.: 846,012

[22] Filed: Apr. 25, 1997

[51] Int. Cl.⁶ .............................. C12N 5/10; C12N 1/00; C12N 15/11; C12N 15/63

[52] U.S. Cl. ...................... 435/325; 435/243; 435/320.1; 435/410; 536/23.1; 536/24.1

[58] Field of Search .................. 536/23.1, 24.1; 435/325, 243, 320.1, 410

[56] References Cited

PUBLICATIONS

Fleury et al, Nature Genetics, vol. 15(3), pp. 269–272, Mar. 1997.

*Primary Examiner*—Terry A. McKelvey

[57] ABSTRACT

The invention relates to regulators of UCP2 gene transcription, including novel UCP2 transcriptional promoters. UCP2 gene promoters are used in diagnosis and pharmaceutical development. In particular, transfected cells comprising UCP2 gene promoters operably linked to a reporter are used in high-throughput pharmaceutical screens.

15 Claims, 1 Drawing Sheet

REGULATORS OF UCP2 GENE EXPRESSION

INTRODUCTION

1. Field of the Invention

The field of this invention is the transcriptional promoter of the UCP2 gene and its use in drug screening.

2. Background

A mitochondrial protein called uncoupling protein (UCP1) is thought to play an important role in the body's regulation of energy utilization. Such regulation provides wide spread physiological controls including body weight, appetite, glucose metabolism, temperature, immune responses, etc.. Mechanistically, UCP1 is thought to create a pathway that allows dissipation of the proton electrochemical gradient across the inner mitochondrial membrane in brown adipose tissue, without coupling to any other energy consuming process (for review, see Nicholis & Locke (1984) Physiol Rev 64, 1–64). Unfortunately, the role of UCP1 in physiologies such as body weight regulation in large adult mammals such as people, cattle, pigs, etc. is likely to be limited, since there is little brown adipose tissue in such animals.

UCP2 is a second, related uncoupling protein that is much more widely expressed in large adult mammals (see, e.g. Fleury et al. (1997) Nature Genetics 15, 269–272 and Tartaglia et al. (1996) WO96/05861). Consistent with a role in the regulation of energy utilization generally, and in diabetes and obesity in particular, the UCP2 gene is upregulated in response to fat feeding and maps to regions of the human and mouse genomes linked to hyperinsulinaemia and obesity. Accordingly, upregulators of this gene hold great therapeutic promise for these diseases. To provide regulators of UCP2 gene expression, we have cloned the endogenous promoter of the human UCP2 gene and identified various deletion mutants having transcriptional regulatory activity.

SUMMARY OF THE INVENTION

The invention provides methods and compositions relating to the UCP2 gene transcriptional promoter. The compositions include recombinant regulators of gene expression comprising the UCP2 promoter of SEQ ID NO:1 or a deletion mutant thereof at least 50 bp in length having cis transcriptional regulatory activity. Exemplary such deletion mutants comprise at lease one of SEQ ID NO:1, bases 411–460, bases 461–510, bases 401–563, bases 319–326, bases 98–104, bases 49–56, bases 49–104 and bases 547–554. In preferred embodiments, the regulators comprise at least one of a GC/SP1, GH-TRE and PR/GR binding site. In further embodiments, the regulators comprise a 5' untranslated UCP2 gene exon. Frequently, the regulators may further comprising a UCP2 or non-UCP2 core promoter operatively joined to said mutant.

The invention also provides hybridization probes and replication/amplification primers having a hitherto novel UCP2 specific sequence contained in SEQ ID NO:1 (including its complement and analogs and complements thereof having the corresponding sequence, e.g. in RNA) and sufficient to effect specific hybridization thereto (i.e. specifically hybridize with SEQ ID NO:1 in the presence of genomic DNA). Such primers or probes are at least 12, preferably at least 24, more preferably at least 36 bases in length.

The invention also provides cells and vectors comprising the disclosed UCP2 regulators, including cells comprising such regulators operably linked to non-UCP2 gene. Such cells find used in the disclosed methods for identifying agents which regulate the activity of a UCP2 promoter. In an exemplary such method, the cells are contacted with a candidate agent, under conditions wherein, but for the presence of said agent, the gene exhibits a first expression; detecting the presence of a second expression of the gene, wherein a difference between said first and said second expression indicates said agent regulates the activity of a UCP2 gene promoter.

The invention also provides other assays for transcriptional regulators including transcription complex formation assays. An exemplary such assay involves combining a DNA comprising a disclosed regulator with a transcription factor and a candidate agent, under conditions wherein, but for the presence of said agent, the regulator and transcription factor form a first association; detecting the presence of a second association of the regulator and transcription factor, wherein a difference between the first and second associations indicates the agent modulates the association of a UCP2 promoter and transcription factor. The subject nucleic acid regulators also find a variety of other applications, including uses in diagnosis. In particular, hybridization probes and PCR primers derived from the disclosed promoters are used to identify genetic mutations in samples comprising a UCP2 gene.

DETAILED DESCRIPTION OF THE INVENTION

Figure 1:
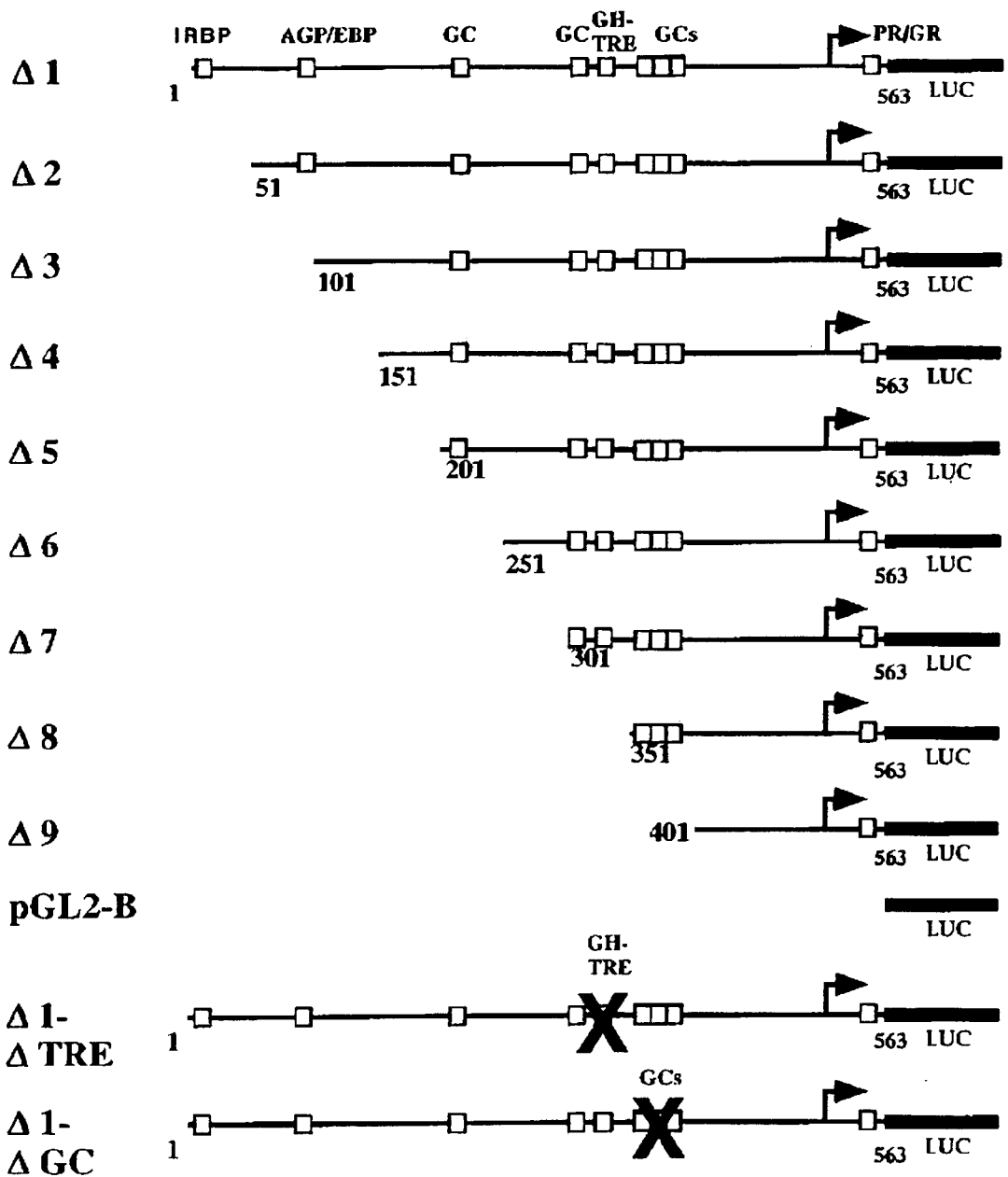
FIG. 1. Diagram of the UCP2 promoter constructs tested for expression of luciferase enzymatic activity in $CaPO_4$ transfected HeLa cells. Cells are harvested 18 hrs post transfection and assayed for luciferase.

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:1 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is sometimes advantageous to use nucleic acids comprising other bases or nucleotide analogs to provide modified stability, etc.

The subject nucleic acids find a wide variety of applications including use as hybridization probes, PCR primers, therapeutic nucleic acids, etc.; use in detecting the presence of UCP2 genes and gene transcripts, in detecting or amplifying nucleic acids encoding additional UCP2 homologs and structural analogs, in gene therapy applications and in a variety of screening assays.

In diagnosis, UCP2-promoter specific hybridization probes find use in identifying wild-type and mutant UCP2 alleles in clinical and laboratory samples. Mutant alleles are used to generate allele-specific oligonucleotide (ASO)

probes for high-throughput clinical diagnoses. In therapy, therapeutic UCP2 nucleic acids are used to modulate cellular expression or intracellular concentration or availability of active UCP2. For example, UCP2 nucleic acids are used to modulate cellular expression or intracellular concentration or availability of active UCP2 protein. UCP2 inhibitory nucleic acids are typically antisense: single-stranded sequences comprising complements of the disclosed natural UCP2 transcript sequences, particularly the untranslated exon 1. Antisense modulation of the expression of a given UCP2 protein may employ antisense nucleic acids operably linked to gene regulatory sequences. Cell are transfected with a vector comprising a UCP2 sequence with a promoter sequence oriented such that transcription of the gene yields an antisense transcript capable of binding to endogenous UCP2 encoding mRNA. Alternatively, single-stranded antisense nucleic acids that bind to genomic DNA or mRNA encoding UCP2 protein may be administered to the target cell, in or temporarily isolated from a host, at a concentration that results in a substantial reduction in expression of the targeted protein. An enhancement in UCP2 expression is effected by introducing into the targeted cell type UCP2 nucleic acids which increase the functional expression of the corresponding gene products. Such nucleic acids may be UCP2 expression vectors, vectors which upregulate the functional expression of an endogenous allele, or replacement vectors for targeted correction of mutant alleles. Techniques for introducing the nucleic acids into viable cells are known in the art and include retroviral-based transfection, viral coat protein-liposome mediated transfection, etc.

The invention provides efficient methods of identifying pharmacological agents or lead compounds for agents active at the level of UCP2 gene transcription. The methods are amenable to automated, cost-effective high throughput screening of chemical libraries for lead compounds. A wide variety of assays for transcriptional regulators are provided including cell-based transcription assays, promoter-protein binding assays, etc. For example, the disclosed luciferase reporter constructs are used to transfect cells such as HeLa cells for cell-based transcription assays. Specifically, HeLa cells are plated onto microtiter plates and used to screen libraries of candidate agents for lead compounds which modulate the transcriptional regulation of the UCP2 gene promoter, as monitored by luciferase expression. An exemplary promoter-protein binding assay is described below. The following examples, exemplary promoter deletion mutants and screening assays are offered by way of illustration and not by way of limitation.

EXAMPLES

Transfection of Cultured HeLa Cells:

Transient transfections were carried out using cultured HeLa cells by calcium phosphate precipitation. 5 ug of promoter-luciferase plasmid DNA were co-transfected with either 1 ug of pMSV expression vector or 1 ug of pMSV-TR expression vector. Samples were co-precipitated with 2 ug of salmon sperm DNA and 0.2 ug of a β-galactosidase internal control expression vector, then applied atop adherent HeLa cells in 6 well tissue culture plates. After 16 hr cells were washed in phosphate buffered saline and refed with fresh DMEM/F12 culture medium supplemented with 10% fetal bovine serum. After an additional 24 hr cells were harvested, lysed and assayed for luciferase and β-galactosidase enzymatic activity according to manufacturer's recommendations (Promega).

Isolation of Human UCP2 Genomic Clones.

Genomic clones containing the promoter region, the first exon and the remaining 5' untranslated region of the human UCP2 gene were obtained by hybridization screening of a bacteriophage 1 library using a PCR amplified probe derived from hUCP2 encoding sequences. The clones were further confirmed by rehybridization using a PCR probe derived from 5' untranslated region sequence, which were obtained from RACE PCR amplification using a primer U5R (ATCGGATCCGAATGGTGCCCATCACACCGCGGTA) (SEQ ID NO:2). Genomic clones were subcloned into pBluescript KSII (Stratagene), and then sequenced using an Applied Biosystems DNA sequencer. The DNA sequence of human UCP2 exon I was identical to the first 100 bp of an EST clone (184239). The promoter sequence was subjected to BLAST search on the NCBI server and found no homolog to any known sequence.

Promoter Sequence Analysis

The DNA sequence of the first untranslated exon and upstream DNA of the mouse UCP2 gene is shown in SEQ ID NO:1. The transcription start site is located at position 461 and exon I proceeds to position 565. A number of transcription factor binding sites are present: GC/SP1 sites are found at positions 200–209, 303–311, 370–379, 383–392 and 395–404. A GH/TRE site is found at positions 319–326; a PR/GR site at positions 546–554; an IRBP site at positions 49–56; and an AGP/EBP site at positions 98–104.

Deletion Mutant Construction and Activity Analysis

The promoter activity of the 5' flanking region of human UCP2 gene and a variety of deletion mutants thereof are conveniently screened in a transient transfection assay using mammalian cell lines. An exemplary assay is the HeLa-cell based luciferase reporter assay of FIG. 1. Selected promoter deletions are amplified by PCR using targeting primers. Amplification primer pairs for exemplified deletions are as follows:

D1: ACTACGCGTGGGTGGGTAGTTTGCCCAGC (SEQ ID NO:3)
ACTAAGCTTCGAGCCGCAGGGAGAACA (SEQ ID NO:4)
D2: ACTACGCGTTGCACTTAAGACACGGCCCC (SEQ ID NO:5)
ACTAAGCTTCGAGCCGCAGGGAGAACA (SEQ ID NO:4)
D3: ACTACGCGTGGAAGGCAAGAGGTGTGTGA (SEQ ID NO:6)
ACTAAGCTTCGAGCCGCAGGGAGAACA (SEQ ID NO:4)
D4: ACTACGCGTTGCCATCCTCACAGAGGTT (SEQ ID NO:7)
ACTAAGCTTCGAGCCGCAGGGAGAACA (SEQ ID NO:4)
D5: ACTACGCGTGGGAGTGGCAAGGGAGTGAC (SEQ ID NO:8)
ACTAAGCTTCGAGCCGCAGGGAGAACA (SEQ ID NO:4)
D6: ACTACGCGTGATGGGACGCACGGAAACGG (SEQ ID NO:9)
ACTAAGCTTCGAGCCGCAGGGAGAACA (SEQ ID NO:4)
D7: ACTACGCGTGCGGGGCGGTCCCCGCGGAA (SEQ ID NO:10)
ACTAAGCTTCGAGCCGCAGGGAGAACA (SEQ ID NO:4)
D8: ACTACGCGTGTAGGAGTGGCAGGCCCGGC (SEQ ID NO:11)
ACTAAGCTTCGAGCCGCAGGGAGAACA (SEQ ID NO:4)
D9: ACTACGCGTCCCCCGAGGCTTAAGCCGCG (SEQ ID NO:12)

ACTAAGCTTCGAGCCGCAGGGAGAACA (SEQ ID NO:4)

The deletions may be recombined in any desired variation. For example internal deletions are readily prepared by amplifying both 5' and 3' deletions followed by ligation. Alternatively, a UCP2 promoter deletion may be fused with non-UCP2 promoter element(s) to form heterohybrid promoters. Internal deletions and heterohybrid constructs are exemplified as follows:

D1 DTRE:

Deletion A) ACTACGCGTGGGTGGGTAGTTTGC-CCAGC (SEQ ID NO:3)
AACGAATTCCCGCGGGGACCGCCCCGCG (SEQ ID NO:13)
PCR then EcoRI and MluI digested Deletion B) AACGAATTCCTGCTCCAGGGTCTCCG-CACCCAA (SEQ ID NO:14)
ACTAAGCTTCGAGCCGCAGGGAGAACA (SEQ ID NO:4)
PCR then EcoRI and HindIII
Triple ligation A+B+pGL2B D1 DGCs:

Deletion C) ACTACGCGTGGGAGTGGCAAGG-GAGTGAC (SEQ ID NO:8)
AACGAATTCCCGGGCCTGCCACTCCTACTT (SEQ ID NO:15)
PCR then EcoRI and MluI digested Deletion D) AACGAATTCCCCCCGAGGCTTAAGC-CGCG (SEQ ID NO:16)
ACTAAGCTTCGAGCCGCAGGGAGAACA (SEQ ID NO:4)
PCR then EcoRI and HindIII
Triple liagation A+B+pGL2B D9-SV40 Core pomoter:

Deletion A) ACTACGCGTGGGTGGGTAGTTTGC-CCAGC (SEQ ID NO:3)
AACGAATTCCCGCGGGGACCGCCCCGCG (SEQ ID NO:13)
PCR then EcoRI and MluI digested The PCR fragments are restriction enzyme digested by MluI and HindIII, and then subcloned into MluI and HindIII sites of pGL-2B or pGL-2P (Promega). Transient transfections are carried out using cultued HeLa cells by calcium phosphate precitation method. After 40 hours, cells are harvested, lysed and assayed for luciferase activity. Exemplary mutants are shown to a range of transcriptional activity (FIG. 1).

Protocol for Thyroid Hormone Receptor (TR)—UCP2 Gene Promoter Binding Assay.

A. Reagents:

Neutralite Avidin: 20 μg/ml in PBS.

Blocking buffer: 5% BSA, 0.5% Tween 20 in PBS; 1 hr, RT.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P TR 10x stock: $10^{-6}$–$10^{-8}$M "cold" TR supplemented with 200,000–250,000 cpm of labeled TR (Beckman counter). Place in the 4° C. microfridge during screening.

Protease inhibitor cocktail (1000x): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

Oligonucleotide stock: (specific biotinylated). Biotinylated oligo at 17 pmole/μl, UCP2 gene promoter containing TRE site: (BIOTIN)-(SEQ ID NO:1, bases 301–350).

B. Preparation of assay plates:

Coat with 120 μl of stock N-Avidin per well overnight at 4° C.

Wash 2× with 200 μl PBS.

Block with 150 μl of blocking buffer.

Wash 2× with 200 μl PBS.

C. Assay:

Add 40 μl assay buffer/well.

Add 10 μl compound or extract.

Add 10 μl $^{33}$P-TR (20,000–25,000 cpm/0.1–10 pmoles/well=$10^{-9}$–$10^{-7}$M final concentration).

Shake at 25C for 15 min.

Incubate additional 45 min. at 25C.

Add 40 μl oligo mixture (1.0 pmoles/40 ul in assay buffer with 1 ng of ss-DNA)

Incubate 1 hr at RT.

Stop the reaction by washing 4× with 200 μl PBS.

Add 150 μl scintillation cocktail.

Count in Topcount.

D. Controls for all assays (located on each plate):

a. Non-specific binding (no oligo added)

b. Specific soluble oligo at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinant regulator of gene expression comprising a nucleotide sequence which consists of nucleotides 1 to 460 of SEQ ID NO:1 or a fragment of said nucleotide sequence which is at least 50 base pairs in length and has cis transcriptional regulatory activity.

2. The regulator according to claim 1, wherein said fragment comprises nucleotides 411 to 460 of SEQ ID NO:1.

3. The regulator according to claim 1, wherein said regulator further comprises nucleotides 461 to 510 of SEQ ID NO:1.

4. The regulator according to claim 1, wherein said regulator comprises nucleotides 401 to 563 of SEQ ID NO:1.

5. The regulator according to claim 1, wherein said fragment comprises nucleotides 319 to 326 of SEQ ID NO:1.

6. The regulator according to claim 1, wherein said fragment comprises nucleotides 98 to 104 of SEQ ID NO:1.

7. The regulator according to claim 1, wherein said fragment comprises nucleotides 49 to 56 of SEQ ID NO:1.

8. The regulator according to claim 1, wherein said fragment comprises nucleotides 49 to 104 of SEQ ID NO:1.

9. The regulator according to claim 1, wherein said regulator further comprises nucleotides 547 to 554 of SEQ ID NO:1.

10. The regulator according to claim 1, wherein said regulator further comprises a non-UCP2 promoter element operatively linked to said regulator.

11. The regulator according to claim 1, comprising a plurality of GC/SP1 binding sites.

12. The regulator according to claim 1, comprising a GH-TRE binding site.

13. The regulator according to claim 1, comprising a PR/GR binding site.

14. The regulator according to claim 1, further comprising a 5' untranslated UCP2 gene exon.

15. A cell comprising the regulator according to claim 1 operably linked to a non-UCP2 gene.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:

( A ) LENGTH: 736 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| GGGTGGGTAG | TTTGCCCAGC | GTAGGGGGGC | TGGGCCCATA | AAAGAGGAAG | TGCACTTAAG | 60 |
| ACACGGCCCC | GCTGGACGCT | GTTAGAAACC | GTCCTGGCTG | GGAAGGCAAG | AGGTGTGTGA | 120 |
| CTGGACAAGA | CTTGTTTCTG | GCGGTCAGTC | TTGCCATCCT | CACAGAGGTT | GGCGGCCCGA | 180 |
| GAGAGTGTGA | GGCAGAGGCG | GGGAGTGGCA | AGGGAGTGAC | CATCTCGGGG | AACGAAGGAG | 240 |
| TAAACGCGGT | GATGGGACGC | ACGGAAACGG | GAGTGGAGAA | AGTCATGGAG | AGAACCCTAG | 300 |
| GCGGGGCGGT | CCCCGCGGAA | AGGCGGCTGC | TCCAGGGTCT | CCGCACCCAA | GTAGGAGTGG | 360 |
| CAGGCCCGGC | CCCGCCCCGC | AGGCCCCACC | CCGGGCCCCG | CCCCGAGGC | TTAAGCCGCG | 420 |
| CCGCCGCCTG | CGCGGAGCCC | CACTGCGAAG | CCCAGCTGCG | CGCGCCTTGG | GATTGACTGT | 480 |
| CCACGCTCGC | CCGGCTCGTC | CGACGCGCCC | TCCGCCAGCC | GACAGACACA | GCCGCACGCA | 540 |
| CTGCCGTGTT | CTCCCTGCGG | CTCGGTGAGC | CTGGCCCCAG | CCCTGCGCCC | TTTGCGCCCC | 600 |
| CCACGCTTGT | TCTGCGTGCG | CTGCCCGCTC | TTCCATTTAC | CTTCTCTCCC | ACCCAAGTTT | 660 |
| GTACTCTTTT | CTTTCTCTCG | GTTTTATTTT | TTGTTTTTGT | TTGTTTGTTT | GAGACAGGCT | 720 |
| TTCGCTCTGT | CTCCCA | | | | | 736 |

( 2 ) INFORMATION FOR SEQ ID NO:2:

( i ) SEQUENCE CHARACTERISTICS:
( A ) LENGTH: 34 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:2:

| | | | | |
|---|---|---|---|---|
| ATCGGATCCG | AATGGTGCCC | ATCACACCGC | GGTA | 34 |

( 2 ) INFORMATION FOR SEQ ID NO:3:

( i ) SEQUENCE CHARACTERISTICS:
( A ) LENGTH: 29 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:3:

| | | | |
|---|---|---|---|
| ACTACGCGTG | GGTGGGTAGT | TTGCCCAGC | 29 |

( 2 ) INFORMATION FOR SEQ ID NO:4:

( i ) SEQUENCE CHARACTERISTICS:
( A ) LENGTH: 27 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:4:

| | | | |
|---|---|---|---|
| ACTAAGCTTC | GAGCCGCAGG | GAGAACA | 27 |

( 2 ) INFORMATION FOR SEQ ID NO:5:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:5:

ACTACGCGTT GCACTTAAGA CACGGCCCC  29

( 2 ) INFORMATION FOR SEQ ID NO:6:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:6:

ACTACGCGTG GAAGGCAAGA GGTGTGTGA  29

( 2 ) INFORMATION FOR SEQ ID NO:7:

( i ) SEQUENCE CHARACTERISTICS:
    ( A ) LENGTH: 28 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:7:

ACTACGCGTT GCCATCCTCA CAGAGGTT  28

( 2 ) INFORMATION FOR SEQ ID NO:8:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:8:

ACTACGCGTG GGAGTGGCAA GGGAGTGAC  29

( 2 ) INFORMATION FOR SEQ ID NO:9:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:9:

ACTACGCGTG ATGGACGCA CGGAAACGG  29

( 2 ) INFORMATION FOR SEQ ID NO:10:

( i ) SEQUENCE CHARACTERISTICS:
    ( A ) LENGTH: 29 base pairs

```
            ( B ) TYPE: nucleic acid
            ( C ) STRANDEDNESS: double
            ( D ) TOPOLOGY: linear ( i i ) MOLECULE TYPE: cDNA ( x i ) SEQUENCE DESCRIPTION: SEQ ID NO:10:

ACTACGCGTG CGGGGCGGTC CCCGCGGAA                                              29

( 2 ) INFORMATION FOR SEQ ID NO:11:

( i ) SEQUENCE CHARACTERISTICS:
            ( A ) LENGTH: 29 base pairs
            ( B ) TYPE: nucleic acid
            ( C ) STRANDEDNESS: double
            ( D ) TOPOLOGY: linear ( i i ) MOLECULE TYPE: cDNA ( x i ) SEQUENCE DESCRIPTION: SEQ ID NO:11:

ACTACGCGTG TAGGAGTGGC AGGCCCGGC                                              29

( 2 ) INFORMATION FOR SEQ ID NO:12:

( i ) SEQUENCE CHARACTERISTICS:
            ( A ) LENGTH: 29 base pairs
            ( B ) TYPE: nucleic acid
            ( C ) STRANDEDNESS: double
            ( D ) TOPOLOGY: linear ( i i ) MOLECULE TYPE: cDNA ( x i ) SEQUENCE DESCRIPTION: SEQ ID NO:12:

ACTACGCGTC CCCCGAGGCT TAAGCCGCG                                              29

( 2 ) INFORMATION FOR SEQ ID NO:13:

( i ) SEQUENCE CHARACTERISTICS:
            ( A ) LENGTH: 29 base pairs
            ( B ) TYPE: nucleic acid
            ( C ) STRANDEDNESS: double
            ( D ) TOPOLOGY: linear ( i i ) MOLECULE TYPE: cDNA ( x i ) SEQUENCE DESCRIPTION: SEQ ID NO:13:

AACGAATTCC CGCGGGGAC CGCCCCGCG                                               29

( 2 ) INFORMATION FOR SEQ ID NO:14:

( i ) SEQUENCE CHARACTERISTICS:
            ( A ) LENGTH: 33 base pairs
            ( B ) TYPE: nucleic acid
            ( C ) STRANDEDNESS: double
            ( D ) TOPOLOGY: linear ( i i ) MOLECULE TYPE: cDNA ( x i ) SEQUENCE DESCRIPTION: SEQ ID NO:14:

AACGAATTCC TGCTCCAGGG TCTCCGCACC CAA                                         33

( 2 ) INFORMATION FOR SEQ ID NO:15:

( i ) SEQUENCE CHARACTERISTICS:
            ( A ) LENGTH: 30 base pairs
            ( B ) TYPE: nucleic acid
            ( C ) STRANDEDNESS: double
            ( D ) TOPOLOGY: linear ( i i ) MOLECULE TYPE: cDNA
```

( x i ) SEQUENCE DESCRIPTION: SEQ ID NO:15:

AACGAATTCC CGGGCCTGCC ACTCCTACTT 30

( 2 ) INFORMATION FOR SEQ ID NO:16:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:16:

AACGAATTCC CCCCGAGGCT TAAGCCGCG 29